(12) United States Patent
Bernard et al.

(10) Patent No.: US 12,357,247 B2
(45) Date of Patent: Jul. 15, 2025

(54) RADIOLOGY DEVICE WITH HELICALLY ARRANGED SOURCES AND DETECTOR

(71) Applicant: THALES, Courbevoie (FR)

(72) Inventors: Guillaume Bernard, Moirans (FR); Guillaume Royer, Moirans (FR)

(73) Assignee: THALES, Courbevoie (FR)

( * ) Notice: Subject to any disclaimer, the term of this patent is extended or adjusted under 35 U.S.C. 154(b) by 272 days.

(21) Appl. No.: 18/033,521

(22) PCT Filed: Oct. 26, 2021

(86) PCT No.: PCT/EP2021/079726
§ 371 (c)(1),
(2) Date: Apr. 24, 2023

(87) PCT Pub. No.: WO2022/090257
PCT Pub. Date: May 5, 2022

(65) Prior Publication Data
US 2023/0404492 A1      Dec. 21, 2023

(30) Foreign Application Priority Data
Oct. 26, 2020   (FR) ...................................... 2010947

(51) Int. Cl.
| A61B 6/03 | (2006.01) |
| A61B 6/02 | (2006.01) |
| A61B 6/06 | (2006.01) |
| A61B 6/40 | (2024.01) |

(Continued)

(52) U.S. Cl.
CPC .............. *A61B 6/032* (2013.01); *A61B 6/027* (2013.01); *A61B 6/06* (2013.01); *A61B 6/4007* (2013.01); *A61B 6/4078* (2013.01); *A61B 6/4275* (2013.01); *G21K 1/025* (2013.01)

(58) Field of Classification Search
CPC ....... A61B 6/032; A61B 6/027; A61B 6/4007; A61B 6/4078; A61B 6/4275; A61B 6/06; G21K 1/025
See application file for complete search history.

(56) References Cited

U.S. PATENT DOCUMENTS

| 4,669,103 A | * | 5/1987 | Barnea ................... A61B 6/032 |
| | | | 378/10 |
| 7,233,644 B1 | * | 6/2007 | Bendahan ............ G01N 23/046 |
| | | | 378/57 |

(Continued)

FOREIGN PATENT DOCUMENTS

WO    2019/011980 A1    1/2019

*Primary Examiner* — Chih-Cheng Kao
(74) *Attorney, Agent, or Firm* — BakerHostetler

(57) ABSTRACT

A radiology device includes a support capable of translational movement about an axis of translation relative to a frame of the device, the support being intended to support an object that is to be imaged, an ionizing-ray generator and a detector configured to detect the rays emitted by the generator, the generator and the detector facing one another. The generator comprises several sources each considered to emit from a focal point, the focal points of the various sources being distributed along a sources axis, the detector extending along a detector axis, the sources axis and the detector axis extending in the form of mutually intertwined helices about the axis of translation.

11 Claims, 6 Drawing Sheets

(51) Int. Cl.
*A61B 6/42* (2024.01)
*G21K 1/02* (2006.01)

(56) References Cited

U.S. PATENT DOCUMENTS

| | | | |
|---|---|---|---|
| 2003/0161434 A1* | 8/2003 | Rand | A61B 6/4085 |
| | | | 378/4 |
| 2005/0111610 A1 | 5/2005 | De Man et al. | |
| 2013/0136229 A1* | 5/2013 | Morton | A61B 6/06 |
| | | | 378/41 |

* cited by examiner

US 12,357,247 B2

RADIOLOGY DEVICE WITH HELICALLY ARRANGED SOURCES AND DETECTOR

CROSS-REFERENCE TO RELATED APPLICATIONS

This application is a National Stage of International patent application PCT/EP2021/079726, filed on Oct. 26, 2021, which claims priority to foreign French patent application No. FR 2010947, filed on Oct. 26, 2020, the disclosures of which are incorporated by reference in their entirety.

FIELD OF THE INVENTION

The invention relates to a radiology device. The invention may be employed in the field of medicine, in industry for performing non-destructive testing and in security for detecting dangerous objects or materials. The invention is of particular use in computed tomography.

BACKGROUND

As is known, computed tomography, also referred to as scanning, employs a system equipped with an x-ray tube emitting a collimated fan-shaped beam known as a "fan beam". The x-ray tube is associated with a detector arranged facing the beam. The tube and the detector rotate about a table receiving the patient. On each revolution, the table advances along the axis of rotation of the tube and of the detector by a small step corresponding to the thickness of a cross section through the patient. Computer processing enables the anatomical structures of the patient to be reconstructed from the 2D cross sections or 3D volume. This system is known as a "CT-scanner", "CT" standing for "Computer Tomography".

The mechanical equipment enabling the tube and the detector to be rotated is bulky and heavy.

The invention seeks to propose a radiology device that can perform computed tomography examinations without the need to employ a tube and a detector that rotate together.

SUMMARY OF THE INVENTION

To that end, the subject of the invention is a radiology device comprising a support capable of translational movement about an axis of translation relative to a frame of the device, the support being intended to support an object that is to be imaged, an ionizing-ray generator and a detector configured to detect the rays emitted by the generator, the generator and the detector facing one another. The generator comprises several sources each considered to emit from a focal point, the focal points of the various sources being distributed along a sources axis, the detector extending along a detector axis, the sources axis and the detector axis extending in the form of mutually intertwined helices about the axis of translation. Each of the sources emits a substantially flat and fan-shaped beam of ionizing rays. The device further comprises a collimator having, facing each source, a slot configured to obtain the fan-shaped beam and produced in a plane of the collimator that is parallel to the axis of translation. The collimator extends mainly along a collimator axis parallel to the sources axis. The slots are not secant. The slots each extend mainly along a curve portion defined in the plane of the collimator and projections, perpendicular to the collimator axis, of curve portions, corresponding to consecutive slots, onto the collimator axis, have a part in common.

Advantageously, the generator and the detector are fixed relative to the frame.

The helical shapes are advantageously positioned relative to one another in such a way that, for each of the sources, a beam of ionizing rays emanating from the source concerned and reaching a portion of the detector is situated substantially in a plane perpendicular to the axis of translation.

The curve portions advantageously follow a substantially sinusoidal shape.

Advantageously, the curve portions comprise at least one straight portion approximating the sinusoidal shape.

Advantageously, the curve portions of the various slots extend parallel to one another.

The detector is advantageously positioned partly between the generator and the axis of translation in a plane perpendicular to the axis of translation while leaving a free space for the passage of the rays emitted by the generator toward the detector.

The helical shape of the sources axis and the helical shape of the detector axis are each advantageously based on a smooth curve centered on the axis of translation.

The smooth curves are advantageously each formed on a cylindrical surface with the cross section of a circle or with the cross section of a regular polygon of which the axis is the axis of translation.

Each source advantageously comprises a cold cathode emitting an electron beam through the field emission technique.

BRIEF DESCRIPTION OF THE DRAWINGS

The invention will be better understood and further advantages will become apparent from reading the detailed description of one embodiment which has been given by way of example, the description being illustrated by the attached drawings in which.

For the sake of clarity, the same elements will bear the same references in the various figures.

DETAILED DESCRIPTION

Figure 1:
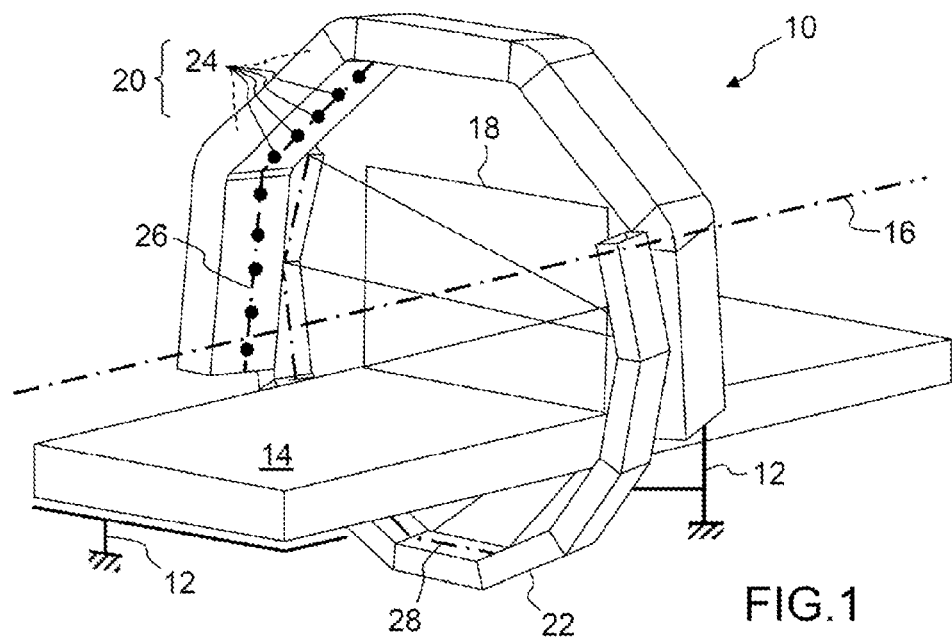
FIG. 1 schematically depicts a radiology device according to the invention.

FIG. 1 depicts a radiology device 10 able to perform computed tomography examinations. The device 10 comprises a frame 12 and a support 14 capable of translational movement relative to the frame 12. The support 14 here takes the form of a tabletop. The support 14 is able to move along an axis of translation 16 relative to the frame 12. A working volume 18 of rectangular cross section is defined above the support 14. The working volume 18 is intended to receive an object that is to be imaged. Any other shape of working volume is also possible, notably a volume of circular cross section. The shape of the support 14 is then adapted accordingly. The device 10 comprises an ionizing-ray generator 20 and a detector 22 which are combined with one another. The generator 20 and the detector 22 are secured to the frame 12. The detector 22 is configured to detect the rays emitted by the generator 20. The generator 20 and the detector 22 face one another so that the detector 22 can receive the ionizing rays emitted by the generator 20.

In order to avoid the need to rotate the generator 20 and the detector 22 about the axis 16, the generator 20 comprises several static ionizing-radiation sources 24 which are distributed about the axis 16. The various sources 24 emit toward the detector 22. The emissions from the sources cross the working volume 18 before reaching the detector 22. As a simplification, it is considered that each of the sources 24 has a focal point from which a beam of ionizing rays extends. In FIG. 1, the focal point of each source also bears the reference 24.

The focal points of the various sources 24 are distributed along a sources axis 26. Further, the detector 22 extends along a detector axis 28. The detector 22 comprises a collection of pixels sensitive to the radiation emitted by the sources, possibly via a scintillator. The pixels are distributed in one or more rows extending along the axis 28.

Figure 2:
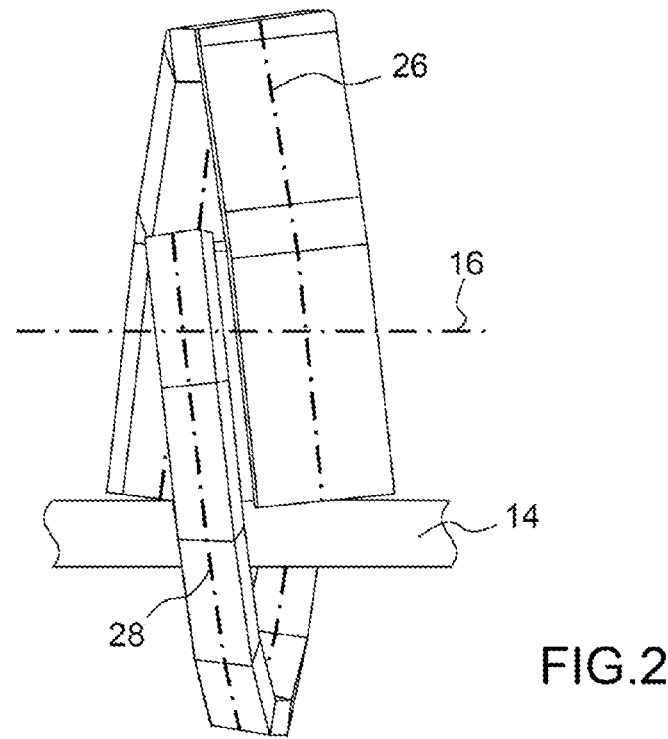
FIG. 2 depicts a profile view of a first embodiment of a combination of a detector and of several sources of the radiology device depicted in FIG. 1.

FIG. 2 depicts a profile view of the generator 20 and the detector 22 which are depicted in FIG. 1. The axis of translation 16 is horizontal in FIG. 2. FIG. 2 makes it easier to illustrate the shapes of the axes 26 and 28. More specifically, the axes 26 and 28 each extend in the form of a helix about the axis of translation 16. The helical shapes of each of the axes 26 and 28 are intertwined in one another. What is meant by intertwined shapes is two helical shapes phase-shifted by 180°, one of them for the generator 20 and the other for the detector 22. In other words, for each point on the generator helix there corresponds a point of the detector helix. These two points are joined by a straight segment perpendicular to the axis of translation 16. The intertwining of the helical shapes allows each of the sources to emit a substantially flat and fan-shaped beam toward the detector 22. The near-flatness of the beam emitted by each of the sources 24 makes it easier for the radiological image to be reconstructed in two or three dimensions. To facilitate the reconstruction of the radiological image, the sources 24 are uniformly distributed along the sources axis 26. The sources 24 of the generator 20 and the detector 22 advantageously cover an angular sector of between 180° and 270° about the axis 16. Again, to facilitate the reconstruction of the radiological image, the helical shapes are advantageously positioned relative to one another such that the beam emanating from a source and reaching a portion of the detector is situated substantially in a plane perpendicular to the axis of translation 16. It is possible for the beam to be inclined with respect to a plane perpendicular to the axis of translation 16, but this makes the reconstruction of the radiological image more complicated. The shorter the pitch of the helix, the more closely the beam will follow the plane perpendicular to the axis of translation 16.

In practice, in order to employ a beam that is completely flat between each of the sources 24 and the detector 22, the sources 24 and the detector 22 would need to be positioned in a plane perpendicular to the axis of translation 16. This is impossible if an angular sector in excess of 180° is to be covered. An intertwined-helix embodiment with a non-zero helix pitch makes it possible to employ a beam of which the shape is slightly sinusoidal as opposed to being perfectly flat. The shorter the pitch of the helices, the flatter this sinusoid will be, which is desirable. Specifically, it is possible to approximate the sinusoid using a straight line, for example using a first-order Taylor series. The shorter the pitch of the helices, the better this approximation is. In order to achieve this objective, the components of the generator 20 and the detector 22 will be chosen so as to reduce this pitch as far as possible.

A helix is a curve of which the tangent at each point makes a constant angle with a given direction, in this instance the direction followed by the axis of translation 16. The helices on which the axes 26 and 28 are based are formed in FIG. 2 on cylindrical surfaces of axis 16 and with the cross section of a polygon approximating to a circle. In FIG. 2, the cylindrical surfaces have the same distance to the axis 16. In the context of the invention, the distances between the axis 16 and the two cylindrical surfaces may differ and may vary notably according to the physical dimensions of each of the sources 24. Likewise, the pitches of the two helices are advantageously the same, which simplifies the reconstruction of the images. For reasons of physical layout of the generator 20 and the detector 22, it is also possible to implement the invention using different helix pitches for the sources axis 26 and the detector axis 28.

Figure 3:
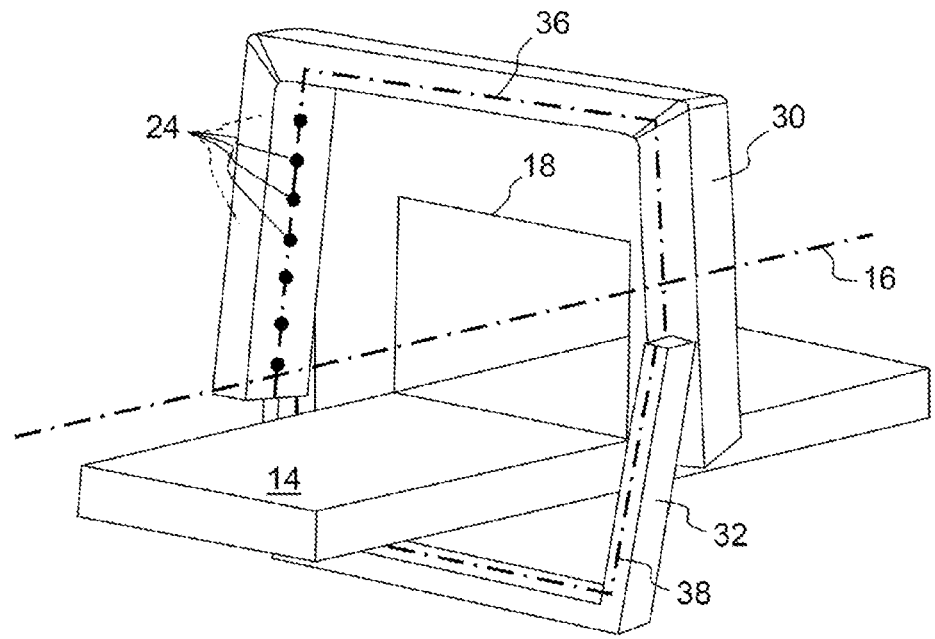
FIG. 3 is a perspective depiction of a second embodiment of a combination of a detector and of several sources of the radiology device depicted in FIG. 1.

FIG. 3 depicts another embodiment of a generator 30 and of a detector 32 which are likewise combined with one another. Like with the generator 20, the generator 30 comprises several sources 24 distributed along a sources axis 36. Further, the detector 32 extends along a detector axis 38. The axes 36 and 38 also each extend in a helical shape about the axis of translation 16. Unlike in FIG. 2, in the embodiment of FIG. 3, the helices on which the axes 36 and 38 are based are formed on cylindrical surfaces of axis 16 and with a substantially rectangular cross section. The straight portions that form the rectangular cross section may make it easier to produce the generator 30 and the detector 32. Any other shape of cylindrical surface on which the sources axis and the detector axis are based is possible within the context of the invention. Different cylindrical surfaces for the sources axis and for the detector axis are also possible. For example, the detector may extend along an axis based on a surface of rectangular cross section while the generator may extend along an axis based on a surface of circular cross section. The cross section may for example be a regular polygon centered on the axis 16. The benefit of a regular polygon, of a circular cross section, or more generally of a smooth curve centered on the axis 16 is that it maintains a substantially constant mean distance between the sources and the detector, and this makes reconstructing the radiological image in two or three dimensions easier.

In practice, the use of helices based on cylindrical surfaces of circular cross section is still the optimal geometric solution for maintaining a constant distance between the sources and the detector. However, it may be easier to produce straight portions as proposed in FIG. 3. The rectangular cross section forms a rough approximation to the circular cross section and cross sections in the form of regular polygons with more than four sides form better approximations.

The sources 24 are advantageously compact as described, for example, in the patent application published as WO 2019/011980 A1 and filed in the name of the applicant company. Each source comprises, inside a vacuum chamber, a cathode emitting an electron beam, and an anode having a target bombarded by the electron beam and emitting a beam of ionizing rays. The cathode advantageously emits the electron beam toward the target using the field emission technique. This type of cathode is also known as a cold cathode as opposed to hot cathodes which are also referred to as thermionic cathodes.

The benefit of employing compact cold-cathode sources is that it allows the helix pitch of the sources axis 26 or 36 to be reduced and allows the focal points of the sources to be brought closer together along the sources axis 26 or 36. Specifically, in conventional computed tomography in which the generator and the detector rotate about the axis of translation, it is possible to create as many images as desired during rotation in order to obtain sufficient data to reconstruct a two- or three-dimensional image. In the invention, by bringing the sources 24 closer together, it is possible to obtain sufficient data without rotating the generator about the axis 16. However, it is possible to incorporate into the radiology device a mechanism enabling rotation either of the generator or of the detector or of both together. Such rotation is desirable for example if the generator does not cover an angular sector of at least 180° about the axis 16. The rotation may cover just a fraction of a full rotation about the axis 16. However, it is still advantageous to produce a radiology device in which the generator 20 or 30 and the detector 22 or 32 are fixed relative to the frame 12 of the device 10.

Figure 4:
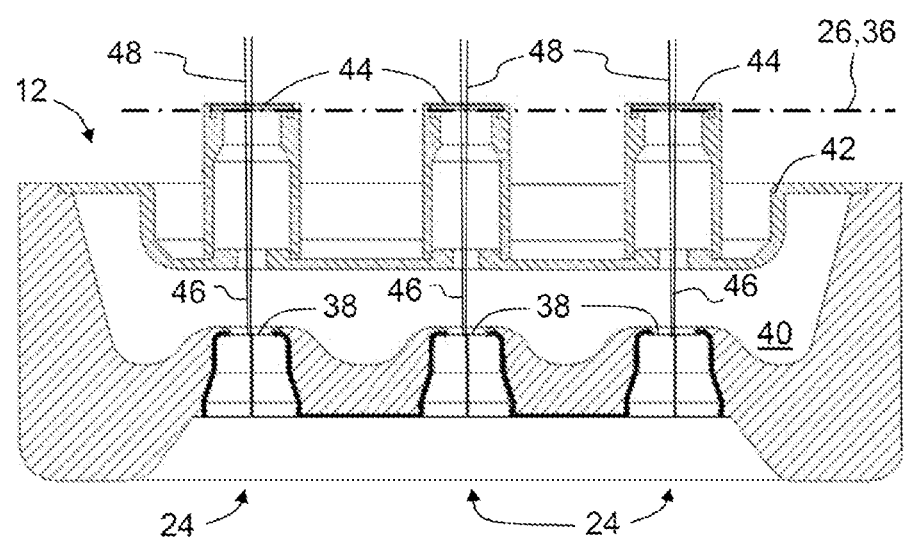
FIG. 4 depicts an example of an ionizing-ray generator that can be employed in a radiology device according to the invention.

FIG. 4 depicts in greater detail a collection of sources 24 having a common vacuum chamber 40. It is notably possible to create all of the sources 24, or at least several of them, in a single vacuum chamber 40. The benefit of a vacuum chamber common to several sources 24 is that it allows the focal points of the beams emitted by each of the sources 24 to be brought closer together. The distribution of the sources 24 along the axis 26 or 36 may be uniform as depicted in FIG. 4, in which the distance separating two adjacent sources 24 is constant. It is also possible to opt for a non-uniform distribution. Alternatively, in the context of the invention, it is of course possible to employ one vacuum chamber per source 24.

In FIG. 4, cold cathodes 38 are distributed parallel to the axis 26 or 36. The sources 24 may comprise an anode 42 that is common to the various sources 24. The anode 42 bears as many targets 44 as there are cathodes 38. Each cathode 38 emits an electron beam 46 toward the target 44 associated with it. The interaction between an electron beam 46 and a target 44 makes it possible to generate a beam of ionizing rays 48. The various sources 24 may be operated independently of one another by controlling their respective cathode 38. In the embodiment described in association with FIG. 3 in which the axis 36 is formed by several straight segments, the sources 24 positioned on the same segment may have a vacuum chamber 40 in common.

Naturally, the invention may also be implemented with thermionic cathode sources. Although generally bulkier than cold-cathode sources, it may be possible to employ them if a greater separation between the sources and a greater helix pitch is acceptable.

Figure 5:
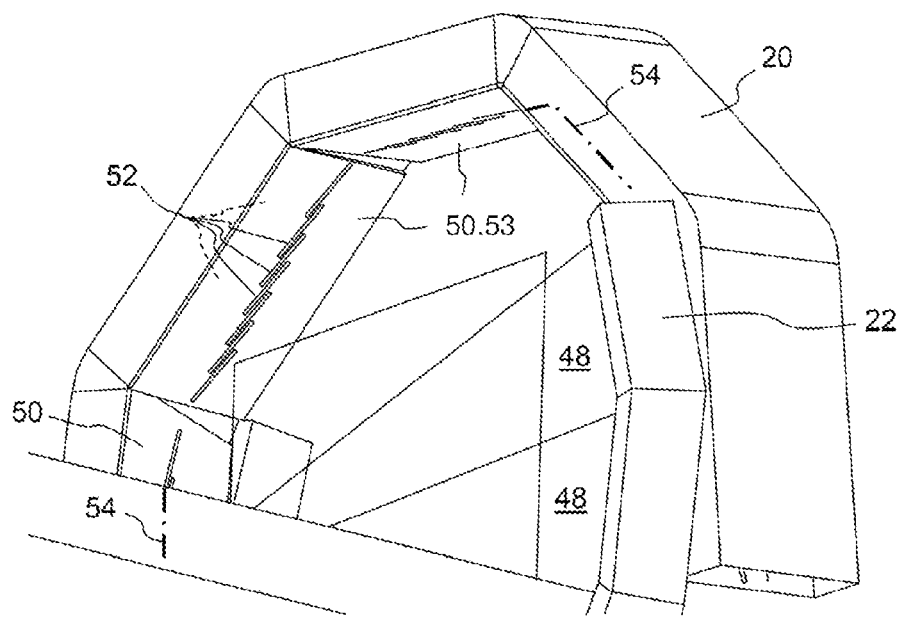
FIG. 5 depicts the combination of a detector, of several sources, and of a first example of a collimator.

FIG. 5 depicts the generator 20 and the detector 22 with both of which there is combined a collimator 50 which, facing each source, has a slot 52 configured to obtain the fan-shaped beam 48. The collimator has one or more planes 53 in which the slots 52 are produced. Each plane 53 is parallel to the axis of translation 16. The planes 53 belong to a cylindrical surface of axis 16. In the variant of FIG. 5, each slot 52 is combined with just one single source 24. The collimator 50 follows the sources axis 26 so that each of the slots 52 faces one single source 24. In other words, the collimator 50 extends mainly along a collimator axis 54 parallel to the sources axis 26. In order not to overload FIG. 5, the sources axis 26, which is hidden by the collimator 50, has not been depicted. The axes 26 and 54 are mutually parallel.

In FIG. 5, the slots 52 associated with the various sources 24 extend mainly along straight line portions parallel to one another. The sinusoid mentioned earlier is approximated to a straight line.

Figure 6A:
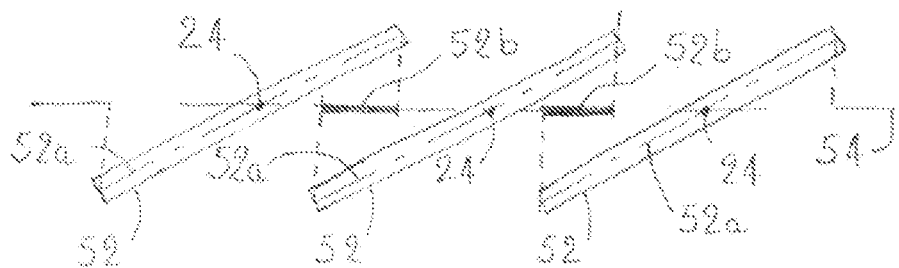
FIGS. 6a, 6b and 6c depict several examples of slot shapes for the collimator of FIG. 5.
Figure 6B:
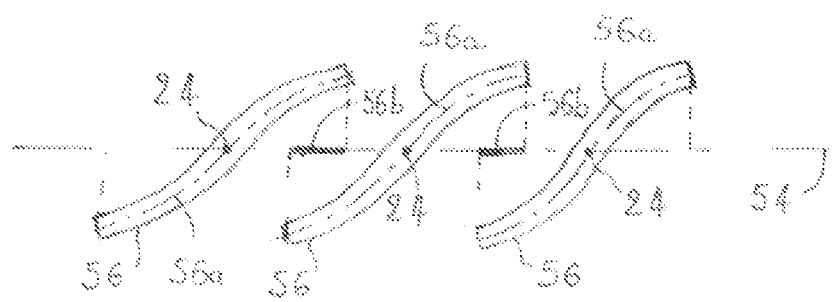
Figure 6C:
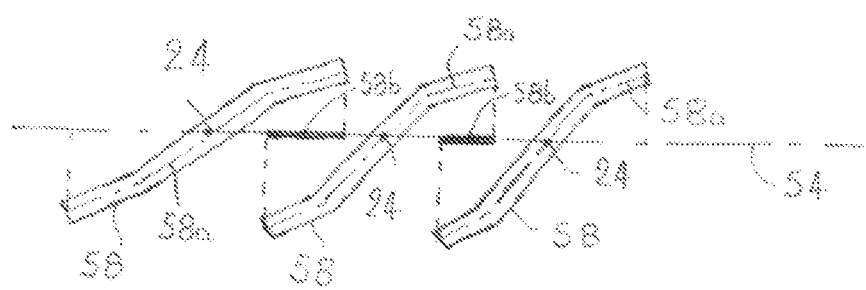

FIGS. 6a, 6b and 6c depict various examples of slot shapes for the collimator which slots are made in one of the planes 53 containing the collimator axis 54 and perpendicular to a plane containing the sources axis 26 and the collimator axis 54. The example of FIG. 6a again depicts the slots 52 visible in FIG. 5. The slots 52 each extend along a straight portion. The example of FIG. 6b depicts slots 56 each extending as a sinusoid portion and the example of FIG. 6c depicts slots each extending along several straight portions forming a broken line. As indicated above, the sinusoid-portion shape is the ideal shape for the slots making it possible to produce the fan beam 48 suited to an intertwined-helix structure for the generator and the detector. However, it is possible to approximate the sinusoidal shape to any shape that allows the fan beams 48 to sweep over the detector. The shapes depicted in FIGS. 6a and 6c are in the straight-portion form and are easier to produce than a sinusoidal shape. The invention may be implemented whatever the number of straight portions employed to approximate a sinusoidal curve.

In general, the various slots 52 or 56 or 58 are mutually parallel. More specifically, in the same collimator, the curves along which the slots mainly extend are mutually parallel. This allows the various fan beams to remain parallel to one another.

In order to ensure that the fan shape of each beam 48 has sufficient angular amplitude, the projections of consecutive slots 52 onto the axis 54 are secant. More specifically, in FIG. 6a, each slot 52 extends mainly along a straight portion 52a. The straight portion enables the creation of the fan beam 48. The length of the straight portion defines the angular extent of the beam 48 concerned. The width of the slot 52, defined perpendicular to the straight portion 52a, gives the thickness of the beam 58 and is very small relative to the length of the straight portion.

It is possible to project, geometrically, in the plane 53, the straight portion 52a onto the axis 54, the projection being done perpendicular to the axis 54. The projections, onto the axis 54, of two straight segments 52a of two consecutive slots 52 have a part in common, identified as 52b in thick line on the axis 54. The same is true in FIG. 6b where each slot 56 extends mainly along a sinusoid portion 56a. The projections onto the axis 54 of sinusoid portions 56a of two consecutive slots 56 have a part 56b in common. In FIG. 6c, each slot 58 extends mainly along a broken line 58a. The projections onto the axis 54 of broken lines 58a of two consecutive slots 58 have a part 58b in common. In general, the slots extend mainly along curve portions defined in the plane 53 and the projections of curve portions corresponding to consecutive slots have a part in common.

Depending on the geometry of the generator 20 and the detector 22 and depending on the desired angular extent for each beam 48, it is possible for the respective projections onto the axis 54 of more than two curve portions corresponding to more than two consecutive slots to have parts in common. However, the straight-portion or sinusoid-portion shape followed by the slots 52 ensures that the slots themselves are not secant. Such a slot shape would be impossible in an embodiment in which the sources were situated in a first plane perpendicular to the axis 16 and in which the detector was situated in a second plane parallel to the plane of the sources. With two parallel planes, one for the sources and the other for the detector, the slots would have a circular-arc shape and would therefore be secant. The intertwined-helix shapes of the axes 26 and 28 make it possible to create adjacent slots of which the projections onto the sources axis 26 overlap, without the slots themselves being secant.

Figure 7:
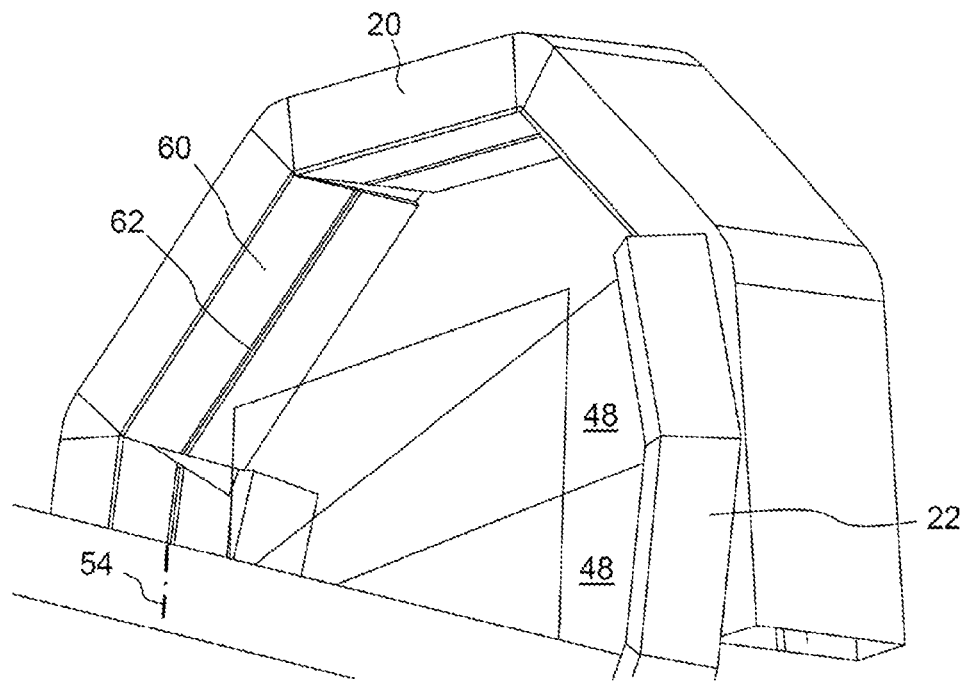
FIG. 7 depicts the combination of a detector, of several sources and of a second example of a collimator.

FIG. 7 depicts a variant collimator 60 comprising a slot 62 associated with several sources 24. Specifically, in the variant of FIG. 5, the slots are close together. By reducing the pitch of the helices, it is possible to approximate the various slots into a single slot extending along the axis 54. In the variant of FIG. 7, the sources axis 26 and therefore the collimator axis 54 are based on a cylinder of axis 16 with the cross section of a regular polygon. Several sources 24 are positioned on the one same side of the polygon. The collimator 60 has a slot 62 per side of the polygon and common to several sources 24 positioned along that same side.

Figure 8:
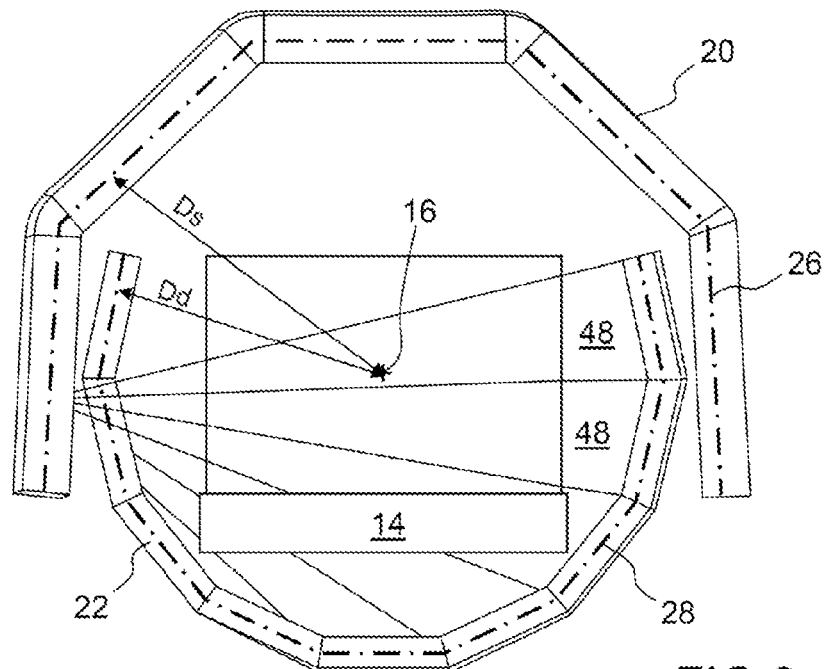
FIG. 8 depicts a variant of a combination of a detector and of a generator offering better intertwining.
Figure 9:
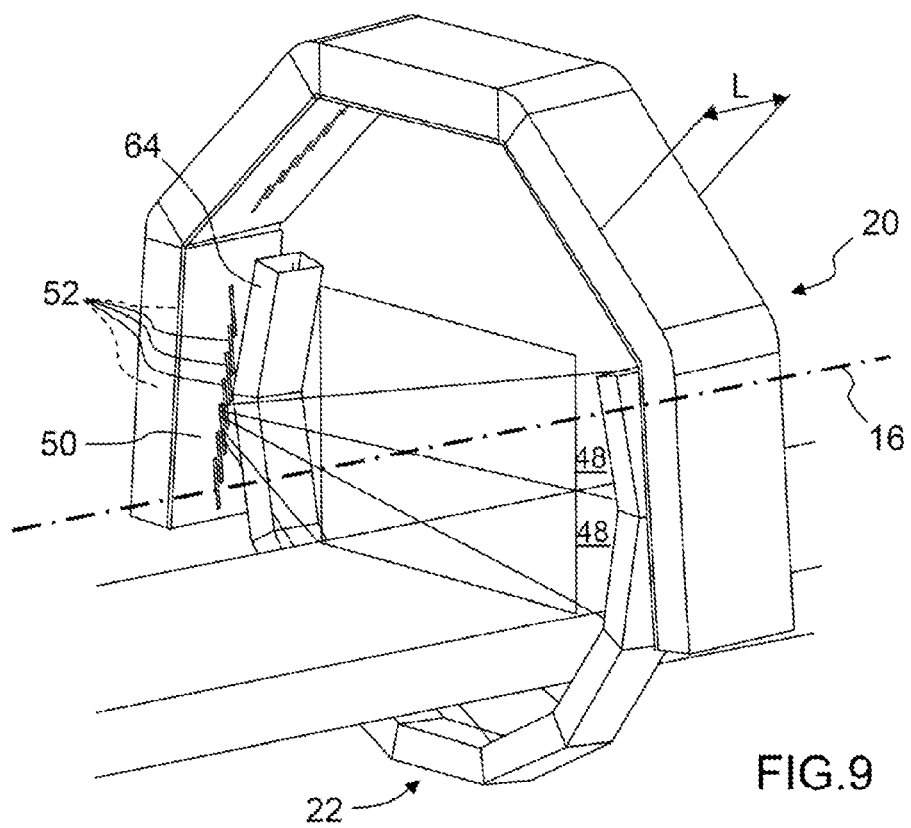
FIG. 9 depicts the detector and the generator of FIG. 7 combined with the collimator of FIG. 5.

FIGS. 8 and 9 depict the combination of a generator 20 and of a detector 22 in which the detector 22 is positioned partly between the generator 20 and the axis 16 in a plane perpendicular to the axis 16 while leaving free space for the passage of the beam 48 emanating from the generator 20 in the region in which the detector 22 masks the generator 20. To allow for this arrangement, the mean distance Ds between the sources axis 26 and the axis 16 is greater than the mean distance Dd from the detector axis 28 to the axis 16. What is meant by mean distance is diameter when the helices of the sources and detector axes 26 and 28 are based on cylinders of circular cross section. When the cross sections of the cylinders are regular polygons, it is possible to define the mean distance as being the mean of the distance from a vertex and of the distance from a side of the polygon. It is possible to achieve this relative arrangement of the generator and of the detector for other, more complex, shapes on which the helices may be based.

This arrangement of the generator and of the detector makes it possible to reduce the pitch of the helices and therefore reduce the separations of the various beams relative to planes perpendicular to the axis 16, making it possible to facilitate the reconstruction of the image. Specifically, the generator may have a great width, the width being defined parallel to the axis 16 and indicated by the reference L in FIG. 8. This width is notably due to the presence of the vacuum chamber 40, one example of which is given in FIG. 4. The sources axis 26 is substantially situated midway across the width of the generator 20. In the variant of FIG. 1 in which the mean distances Ds and Dd are substantially equal, one of the lateral faces of the detector 22 has to be distant from the sources axis 28 by at least half the width L. In the variant of FIGS. 8 and 9, it is possible to bring the lateral face 64 of the detector 22 closer to the sources axis 28 while still allowing the beam 48 to spread without touching the detector 22 and notably the lateral face 64 thereof. A collimator 50 is depicted in FIG. 8.

In FIGS. 8 and 9, the detector 22 is depicted as being closer to the axis 16 than the generator 20. The reverse is equally possible, in order to reduce the pitch of the helices. However, the layout of FIGS. 8 and 9 offers the advantage of improving the quality of the images formed by the device. Specifically, with this layout, the detector 22 is as close as possible to the working volume, meaning that there is less dispersion of the beam once it has crossed the working volume 18.

The invention claimed is:

1. A radiology device comprising a support capable of translational movement about an axis of translation relative to a frame of the device, the support being intended to support an object that is to be imaged, an ionizing-ray generator and a detector configured to detect the rays emitted by the generator, the generator and the detector facing one another, wherein the generator comprises several sources each considered to emit from a focal point, the focal points of the various sources being distributed along a sources axis, in that the detector extends along a detector axis, in that the sources axis and the detector axis extend in the form of mutually intertwined helices about the axis of translation, in that each of the sources emits a substantially flat and fan-shaped beam of ionizing rays, in that the device further comprises a collimator having, facing each source, a slot configured to obtain the fan-shaped beam and produced in a plane of the collimator that is parallel to the axis of translation, in that the collimator extends mainly along a collimator axis parallel to the sources axis, in that the slots are not secant and in that the slots each extend mainly along a curve portion defined in the plane of the collimator and in that the projections, perpendicular to the collimator axis, of curve portions, corresponding to consecutive slots, onto the collimator axis, have a part in common.

2. The radiology device as claimed in claim 1, wherein the generator and the detector are fixed relative to the frame.

3. The radiology device as claimed in claim 1, wherein the helical shapes are positioned relative to one another in such a way that, for each of the sources, a beam of ionizing rays emanating from the source concerned and reaching a portion of the detector is situated substantially in a plane perpendicular to the axis of translation.

4. The radiology device as claimed in claim 3, wherein the curve portions follow a substantially sinusoidal shape.

5. The radiology device as claimed in claim 4, wherein each curve portion comprises at least one straight portion approximating the sinusoidal shape.

6. The radiology device as claimed in claim 1, wherein the curve portions of the various slots extend parallel to one another.

7. The radiology device as claimed in claim 1, wherein the detector is positioned partly between the generator and the axis of translation in a plane perpendicular to the axis of translation while leaving a free space for the passage of the rays emitted by the generator toward the detector.

8. The radiology device as claimed in claim 1, wherein the helical shape of the sources axis and the helical shape of the detector axis are each based on a smooth curve centered on the axis of translation.

9. The radiology device as claimed in claim 8, wherein the smooth curves are each formed on a cylindrical surface with the cross section of a circle of which the axis is the axis of translation.

10. The radiology device as claimed in claim 8, wherein the smooth curves are each formed on a cylindrical surface with the cross section of a regular polygon of which the axis is the axis of translation.

11. The radiology device as claimed in claim 1, wherein each source comprises a cold cathode emitting an electron beam through the field emission technique.

* * * * *